United States Patent [19]

Snedecor et al.

[11] Patent Number: 5,055,399
[45] Date of Patent: Oct. 8, 1991

[54] ENZYMATIC SYNTHESIS OF ALPHA-L-ASPARTYL-L-PHENYALANINE LOWER ALKYL ESTERS

[75] Inventors: Bradley R. Snedecor, Brisbane; Chung C. Hsu, Walnut Creek, both of Calif.

[73] Assignee: Genentech, Inc., South San Francisco, Calif.

[21] Appl. No.: 347,464

[22] Filed: May 4, 1989

Related U.S. Application Data

[62] Division of Ser. No. 691,689, Jan. 15, 1985, abandoned.

[51] Int. Cl.$^5$ .................... C12P 21/00; C07C 229/00
[52] U.S. Cl. ........................................ 435/68.1; 560/40
[58] Field of Search ........................... 435/68.1; 560/40

[56] References Cited

U.S. PATENT DOCUMENTS

| | | | |
|---|---|---|---|
| 3,972,773 | 8/1976 | Isowa et al. | 435/68.1 |
| 4,017,472 | 4/1977 | Farkas et al. | 530/801 |
| 4,092,219 | 5/1978 | Lin et al. | 535/68.1 |
| 4,119,493 | 10/1978 | Isowa et al. | 435/68.1 |
| 4,256,836 | 3/1981 | Isowa et al. | 435/68.1 |
| 4,426,323 | 1/1984 | Jain | 530/351 |
| 4,427,658 | 1/1984 | Maubois et al. | 435/68.1 |
| 4,532,207 | 7/1985 | Brewer et al. | 435/68.1 |
| 4,710,583 | 12/1987 | Chmurny et al. | 435/68.1 |
| 4,810,817 | 3/1989 | Chmurny et al. | 560/40 |
| 4,959,350 | 9/1990 | Frokjaer et al. | 514/2 |
| 5,002,871 | 3/1991 | Iacobucci | 435/68.1 |

*Primary Examiner*—Douglas W. Robinson
*Assistant Examiner*—Michael Meller
*Attorney, Agent, or Firm*—Janet E. Hasak

[57] ABSTRACT

Enzyme-catalyzed synthetic reactions having otherwise unfavorable equilibria are facilitated by recovery of polypeptides by electrodialysis. A process of preparing polypeptides is provided that can be operated continuously to produce high yields of enriched polypeptides without recourse to post-synthetic product manipulations heretofore employed that are expensive and present a risk of residual toxic by-products. The invention is applied to advantage in the preparation of alpha-L-aspartyl-L-phenylalanine lower alkyl esters.

10 Claims, 2 Drawing Sheets

ENZYMATIC SYNTHESIS OF ALPHA-L-ASPARTYL-L-PHENYLALANINE LOWER ALKYL ESTERS

This application is a division of application Ser. No. 06/691,689, filed Jan. 15, 1985, now abandoned.

BACKGROUND

This application relates to enzymatic synthesis of compounds, particularly low molecular weight peptides containing from 2 to 10 amino acid residues. It relates specifically to the synthesis of alpha-L-aspartyl-L-phenylalanine lower alkyl esters.

One of such esters, the methyl ester (hereinafter APM), is commonly known as aspartame, a powerful sweetening agent. It is comprised of L-phenylalanyl methyl ester linked through a peptide bond to an L-aspartyl residue.

APM has been synthesized by many methods, including directly reacting L-phenylalanine methyl ester and an N-protected aspartic acid anhydride, or by enzymatically joining N-protected L-aspartic acid and an L-phenylalanine methyl ester. A modification of this enzymatic method, which does not require the use of N-protected L-aspartic acid, is further described by Harada et al., EPA 74,095. In the method of Harada et al. a culture of certain enumerated microorganisms is contacted with L-aspartic acid and a methyl ester of L-phenylalanine in order to synthesize APM. In the Examples, the microorganisms were cultured and suspended in a medium containing L-aspartic acid and L-phenylalanine methyl ester, APM was allowed to accumulate, the cells were separated from the medium and the supernatant medium thereafter was subjected to fractionation. The APM recovery ranged from 1.2 to 7.5 g (adjusted on the basis of one liter of culture medium). Molar yields ranged from 0.5 percent to 1.4 percent based on the amount of phenylalanine methyl ester added to the reaction mixture.

The peptide yields obtainable by the Harada et al. enzymatic synthesis are limited by the equilibrium of the enzyme-catalyzed reaction, which tends to favor the amino acid reactants rather than the dipeptide product. Extensive efforts have been devoted to improving the equilibrium in favor of the synthetic product (Oyama et al., "Chemtech", February 1984, pp 100–105). Sparingly soluble peptidyl products are favored in the equilibrium, but not all peptides have such characteristics or, if such characteristics are introduced, they may be difficult and expensive to remove from the final product. For example, carbobenzoxylated (N-blocked) L-aspartic acid and L-phenylalanine methyl ester have been enzymatically conjugated to yield an insoluble addition compound (Isowa et al., U.S. Pat. No. 4,436,925). This method is disclosed to result in product yields of up to 99.1 percent at the immediate conclusion of fermentative synthesis. However, additional steps are required to remove the benzoylcarbonyl moiety and the potential exists for product contamination by the L-aspartic acid derivative.

Water-miscible or immiscible organic solvents have been used in attempts to improve the yields of synthetic protease reactions. These methods are unsatisfactory because many organic solvents inhibit protease activity and the products must be separated from the solvent by expensive processes. Also, the solvent can be costly, and must be efficiently recycled.

Notwithstanding such efforts to secure highly efficient synthesis of contaminant-free products, the art has failed to assemble an economical system for enzymatic peptide synthesis. Heretofore, the art has necessarily traded-off increased yields in the enzyme catalyzed step against requirements for further processing of the reaction product, including the removal of potentially toxic substances. Accordingly, the objects of this invention include synthesizing peptides in high yield from ordinary microbial cultures or immobilized enzymes, but without the need either to later remove product substituents or otherwise undertake covalent modifications of the product peptide, or to purify the product from organic solvents. These and other objects of this invention will be apparent from consideration of this application as a whole.

SUMMARY

The objects of this invention are accomplished by a process comprising (a) contacting one or more reactants with an enzyme to produce a composition comprising a mixture of said reactants and one or more products, wherein either all of the products or all of the reactants bear substantially zero net ionic charge, provided that if all reactants bear substantially zero net ionic charge then the products bear a substantial net ionic charge, or if all products bear substantially zero net ionic charge then the reactants bear a substantial net ionic charge;

(b) electrodialyzing the composition of step (a) whereby product is separated from reactant;

(c) recovering product; and (d) recycling separated reactant into contact with the enzyme.

This process is accomplished by an apparatus comprising an immobilized enzyme in fluid communication with a means for electrodialysis, means for recirculating reactant from the electrodialysis means to the immobilized enzyme, and means for recovering product from the electrodialysis means. The electrodialysis means generally comprises a stack of spacer-separated alternating anion and cation exchange membranes which are sandwiched between an anode and cathode, and means for applying voltage across the stack of membranes. In one embodiment the enzyme is immobilized within the electrodialysis means on the salt-accumulating side of the membranes in order to take advantage of the localized concentration of the charged components of the reactant-product system. In another embodiment, which is preferred, the enzyme is immobilized in a reaction chamber outside of the electrodialysis means but in direct or indirect fluid communication therewith.

Additionally provided is an electrodialysis apparatus having salt accumulating and depleting cells, means for introducing charged reagents into the salt accumulating cell, means for removing product from the salt depleting cells, an enzyme immobilized in the salt accumulating cell in the region of highest concentration of charged ions and non-electrically conductive means for recycling fluid from the salt accumulating cell into the salt depleting cell.

BRIEF ESCRIPTION OF THE DRAWINGS

FIG. 1 depicts the preferred embodiment of an apparatus for practicing the inventive method on a continuous basis. A reactor containing an enzyme is placed in fluid communication with a two stage set of electrodialysis devices, the principal function of one of which is to remove accumulated inorganic salt and of the other to remove reactants from the product stream. The apparatus provides means for recycling reactants to the reactor and for product recovery.

FIG. 2 illustrates an alternative embodiment of the apparatus.

DETAILED DESCRIPTION

Figure 1:
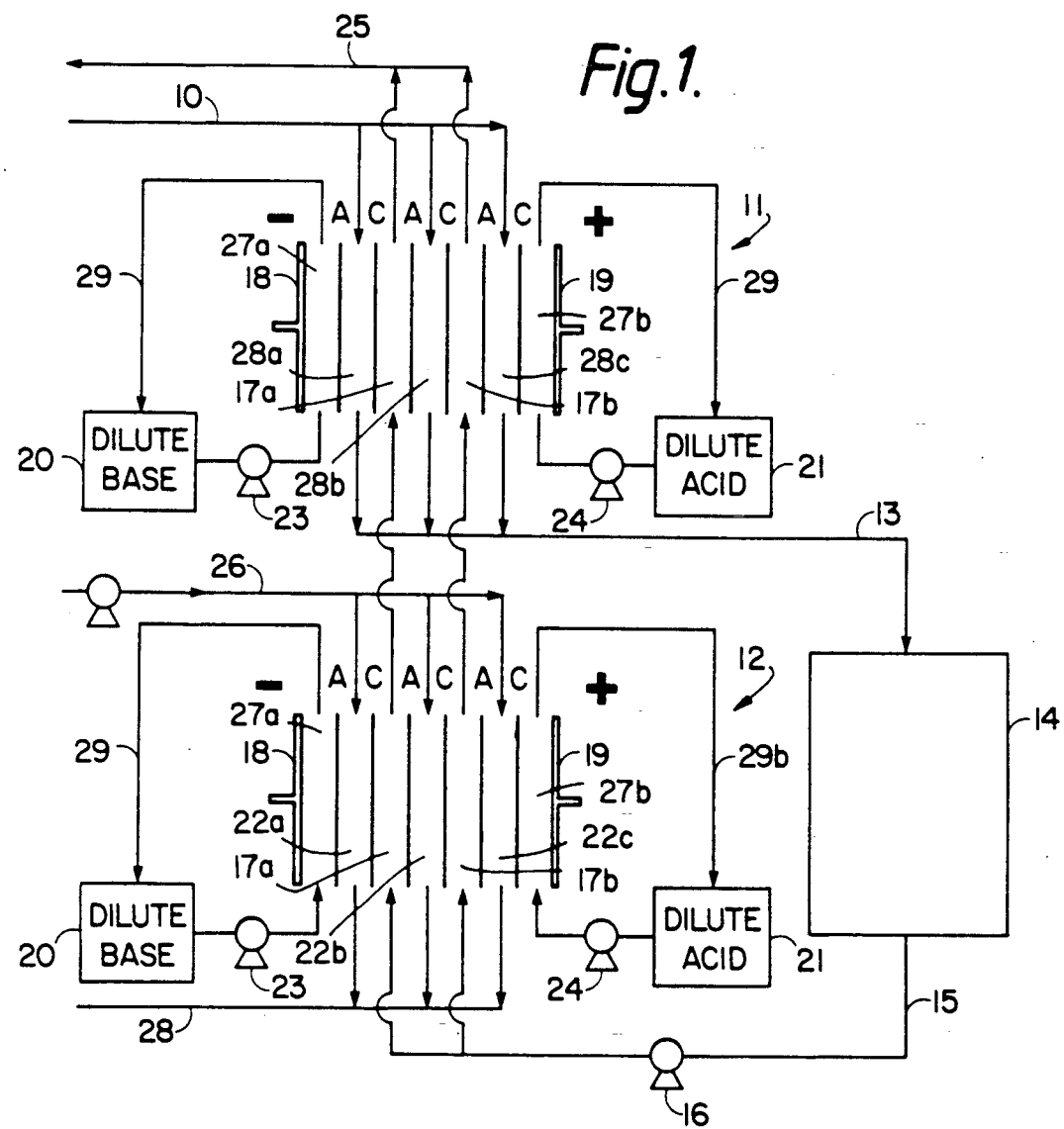

The method of this invention is ordinarily employed to synthesize compounds having a peptide bond, although it can be used to drive any enzymatic reaction having an equilibrium that does not favor product to the desired degree. An enzyme is selected that is capable of catalyzing the synthesis of peptide bonds from carboxyl- and amino-bearing reactants. Furthermore, the products and reactants must have a sufficiently different net ionic charge that they can be separated by electrodialysis, and in addition either one of the class of products or reactants must bear substantially no net charge. A considerable number of systems have been described which meet these criteria. For example, see M. Bergman et al., "Adv. Enzymol." 1:63 (1941). The reactants generally are amino acids, although the amino acids chosen are not limited to the 21 amino acids normally found as protein constituents but may include derivatives thereof such as esters. Suitable starting amino acids and final products are described in U.S. Pat. No. 4,256,836, the disclosure of which is incorporated by reference, except that it is preferred that the amino group of the dicarboxylic amino acid be unsubstituted. Mixtures of L and D amino acids also are used, as they are less expensive starting reactants. However, it is preferred to use purified L stereoisomers because D amino acids may competitively inhibit proteolytic enzymes. In addition, the amino or carboxyl reactant may be a protein or a low molecular weight polypeptide. Here, the enzyme used for the final synthesis step will be a peptidase which is not substrate specific for endoproteolytic cleavage of the starting polypeptide and therefore will not hydrolyze the polypeptide substrate in competition with the amino acid addition reaction. When the desired reaction is the synthesis of a dipeptide, i.e., a compound containing a single peptide bond, the enzyme catalyst preferably will be an exopeptidase. The preferred starting materials for APM are L-aspartic acid and L-phenylalanine methyl ester.

The enzyme which is used for coupling the reactants is capable of catalyzing the formation of peptide or amide bonds. It is isolated from microorganisms or vertebrate cells that ordinarily synthesize the enzyme. Desirably, the enzyme is selected for resistance to the elevated substrate (reactant) and organic solvent concentrations that may be encountered in some peptide synthetic systems, as these are conditions that will aid in driving the forward reaction. Also, the enzyme should act on unblocked substrates, for the reasons discussed above.

Suitable enzymes include carboxyl hydrolases, in particular exoproteases, endoproteases, esterases and lactamases, including serine (alkaline) proteinases such as alpha-chymotrypsin, trypsin and subtilisin; thiol proteinases such as papain; carboxyl (acidic) proteinases, e.g. pepsin; and metalloproteinases (neutral proteinase) such as thermolysin, prolisin, tacynase N or dispase. Enzymes from the EC 3.4.21, 3.4.22, 3.4.23 and 3.4.24 classifications of the Nomenclature Committee of the International Union of Biochemistry are useful. The enzymes described in Harada et al. and Isowa et al. (both op cit.) are preferred for the synthesis of APM. Enzymes to be used for the synthesis of other peptides generally will be different since enzymes having different substrate specificity than for APM will be required.

The enzyme need not be purified before use, i.e., it may be present in living or killed cells, or it may be cell-free and purified to the desired degree. The cells or enzyme composition should be free of interfering enzymes, i.e., undesired esterases, proteases or the like that might modify the starting materials or the synthetic product in undesired ways. For example, the synthetic enzyme used in APM synthesis should be free of esterase that is capable of hydrolyzing L-phenylalanine methyl ester. The use of mixtures of enzymes which catalyze desirable sequential reactions is within the scope herein. The products of all initial synthetic steps prior to the last step in which final product is synthesized preferably will bear a net ionic charge so as to avoid coelectrodialysis of intermediates with the final product. Obviously, the use of neutral reactants and a charged final product is satisfactory.

Generally the enzyme catalyzed synthetic reaction is conducted in a reaction chamber separate from the product separation function. In these embodiments the most economical approach is to leave the enzyme in the microbial cells which produce it. The cells preferably are killed before use rather than being used as a living culture. The hollow fiber reactor system described in J. Kan et al., "Biotechnology and Bioengineering" 20: 217–230 (1978) is preferred. In all embodiments of the invention it also is acceptable to produce the enzyme in a cell free state and thereafter immobilize it by entrapment or by covalent cross-linking or ionic adsorption to a support matrix or membrane. Methods for immobilizing enzymes are described in B. Abbott, "Adv. Appl. Microbiol." 20: 203–257 (1976); B. Sharma et al., "Angew. Chem., Int. Ed. Engl." 21: 837–854 (1982); L. Wingard et al., *Applied Biochemistry and Bioengineering*, Vol I, pp329–357 (1976); and T. Jack et al., *Adv. Biochem. Eng.*, Vol 5: 125–145 (1977). One skilled in the art will select the optimal approach by routine screening.

The preferred apparatus of this invention is shown in FIG. 1. Conduit 10 supplies a mixture of reactants from a storage reservoir (not shown) to chambers 28a, 28b and 28c of the first electrodialysis device shown generally at 11. It is desirable to make provisions for pH control by, for instance, including a buffer in the mixture of reactants supplied by conduit 10, or by using a multiplicity of devices 11 in a staged configuration with pH control between stages. The reactant solution passes through device 11 as indicated at 28a, 28b and 28c where it is enriched in reactants which have been removed from the product stream in chambers 17a and 17b of device 11. The reactant stream, enriched in recycled reactants, is pumped (pump not shown) via conduit 13 into enzyme reactor chamber 14. Conduit 15 communicates with electrodialysis cell 12 under the control of pump 16. It transports the solution exiting the enzyme reactor. This solution, termed the product solution because it serves as the vehicle for product removal, contains at this point both product and unconsumed reactants.

Each of the electrodialysis devices 11 and 12 contain chambers 17a and 17b through which product solution passes. In each device, dilute basic and acidic solutions are recirculated through chambers 27a and 27b and conduits 29a and 29b from reservoirs 20 and 21, respectively, under the control of pumps 23 and 24, respectively. A source of direct voltage (not shown) is applied across the ion exchange membranes, designated C for cation and A for anion exchanging, by way of cathode 18 and anode 19. In the case of device 11 chambers 28a, 28b and 28c collect the unconsumed, ionically charged reactants while product, which is relatively uncharged, remains in chambers 17a and 17b and exits via conduit 25 to a product collection site (not shown). The purpose of device 12 is largely to remove inorganic salts which accumulate in the system, as well as to remove some water. Conduit 26 supplies a dilute salt solution to chambers 22a, 22b and 22c, and a solution containing electrodialyzed salt is removed through conduit 28. Loss of charged reactants in device 12 is minimized by employing ion exchange membranes having a relatively small pore size, i.e., which are permeable to ions under about 200–300 MW. In contrast, the device 11 membranes are permeable to ions having a molecular weight less than about 1000 so that generally only inorganic ions are purged from the system in device 12 while reactants are removed from the product stream in device 11. Desalting device 12 is not essential to the successful use of the process herein, but it is desirable for long-term continuous operation of the system because elevated salt concentrations may have an adverse effect on the enzyme in the reactor 14.

Figure 2:
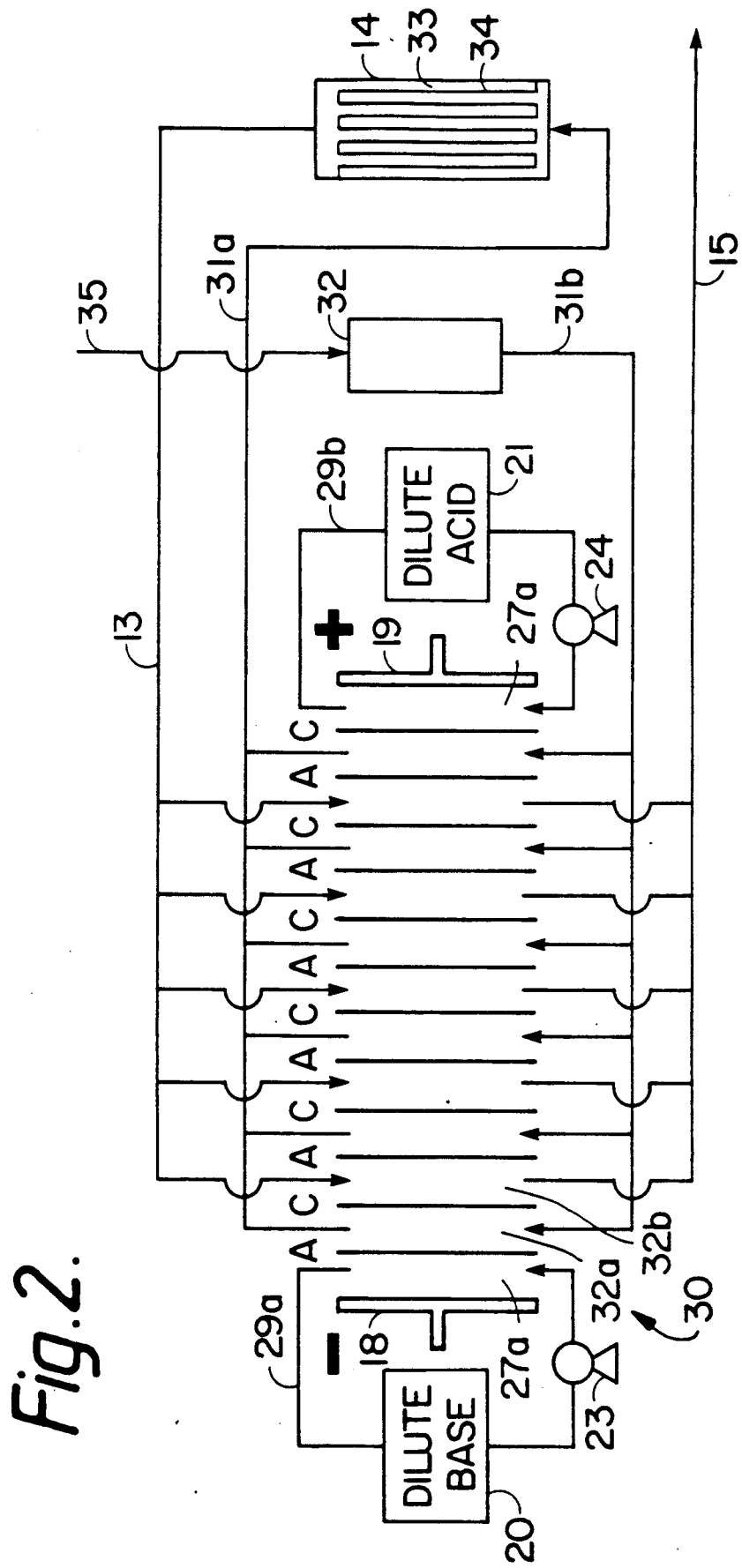

Another suitable apparatus for the enzymatic synthesis and recovery of APM is shown in FIG. 2. It consists of two principal elements, an electrodialysis device generally shown at 30 and a hollow fiber enzyme reactor 14.

The electrodialysis device is an Ionics Medimat 110 brand electrodialysis apparatus modified to carry out separation of APM from sodium aspartate (SA) and phenylalanine methyl ester (PME) HCl. The membrane stacking arrangement used with the electrodialysis apparatus is shown in FIG. 2. It is an alternating stack of anion permeable and cation permeable membranes in which the cation permeable face of the stack is oriented toward the anode. It contains a number of cells (spaces bound by ion exchange membranes). The number of cells is not critical and can be considerably larger than as shown in the Figs. Further, it is not critical to use alternating anion and cation exchange membranes. The cation permeable membrane is an Ionics CZL386, a sulfonate group-substituted membrane reinforced with a copolymer of vinyl chloride and acrylonitrile. This membrane (CZL) has a molecular weight cut-off of about 200–300, i.e., which readily passes substances with molecular weights below 200–300 MW. The anion permeable membrane, Ionics QZL386, is similar but substituted with quaternary ammonium groups. The cation transfer membrane will permit the transfer of cations while excluding anions, and vice versa in the case of the anion transfer membrane. Reservoirs of dilute acid (0.1M $H_2SO_4$) and dilute base (NaOH 0.1N), respectively designated 21 and 20, supply acid and base to the electrodialysis cell generally shown at 30 through conduits 29a and 29b under the control of pumps 24 and 23 respectively. Each chamber was bounded by ion exchange membranes on the sides separated by spacers (not shown) through which passages lead to the conduits 15, 13, 31a or 31b.

The enzyme reactor 14 containing enzyme (shown as a stippled area 33) was as described in J. Kan et al, op cit., except that the cells located on the shell side of the hollow fiber dialyzer were *Pseudomonas putida* described in Harada et al., op cit.

When current flows between the electrodes cation exchange membranes will allow cations to migrate through the membranes under the influence of the electric field while anions that migrate in the opposite direction will be largely prevented from crossing the membrane. On the other hand, anion exchange membranes will allow anions to cross while largely preventing cations from crossing. When an alternating array of cation-exchange and anion-exchange membranes is used every other compartment bounded by these membranes will accumulate ions. The solution in the remaining compartments will be depleted of ions (the "salt depleting" chambers or cells) but will contain uncharged substances such as APM. Generally, and specifically in the case of APM, the reactor effluent to be treated is passed through the salt depleting compartment, and a solution in which the charged species will accumulate is passed through the others, termed "salt accumulating". Generally, the solutions passed directly between the electrodes and the entire stack of cells (chambers 27a, for example) are kept separate from the process streams. The effluent stream from the enzyme reactor is thus separated into two solutions, one enriched in product and one enriched in reactants. The solution stream enriched in reactants is fed back into the enzyme reactor and the solution stream enriched in product is led away from the reactor system. Thus the reactants are constantly circulated between an enzyme or cell reactor and an electrodialysis stack, while product is continuously being removed from the combined system.

In contemplated operation the device was equilibrated with a dilute solution of SA and PME before use. During steady state operation the product stream exiting the enzyme reactor 33 at conduit 13 contained about 40 g/l SA, about 66 g/l of PME and about 3.4 g/l of APM at an adjusted pH of about 5.65. The reactant and water loss make-up stream is transported through conduit 35 and into reservoir 32 and thence via conduit 31b to device 30. The flow rates of the product stream in conduit 15 and salt accumulating stream in conduit 31a were set for steady state operation through each pair of cell chambers, two of which are shown for example at 32a and 32b. The flow rate of the electrode streams was about 500 ml/min/each cell.

Electrodes 18 and 19 were connected to a source of direct current (not shown). The voltage was set at about 3 volts/cell pair. The product and salt accumulating streams were pumped through conduits 15 and 31a, respectively. First the sodium and chloride, then aspartate and PME ions, were removed from the product stream. Continuous operation produced a product stream containing essentially no SA or PME and an APM concentration of about 7 g/l. An occasional salt purge is desirable.

An additional advantage from the use of this device, is that the product solution is concentrated by electroosmosis. If the desired product is concentrated to a point near saturation it may be precipitated in a step downstream from the electrodialysis cell, e.g., by cooling the solution during passage through a heat exchanger (not shown), and then separation of the precipitate by conventional methods, e.g., by recovery from a continuous centrifuge (not shown).

An alternative, but less preferred embodiment would have the enzyme located in direct contact with the product solution rather than being separated from the solution by a hollow fiber or other dialysis membrane as shown at 34 in reactor 14. Instead, the enzyme-containing cells or cell-free enzyme are immobilized in accordance with T. Jack et al., op cit. (for example by covalent linkage of the cells to activated agarose) or L. Wingard et al., op cit. (for example by covalent bonding of cell-free enzyme to diazotized arylamino glass or, preferably, chloro, bromo or iodo cellulose, or by noncovalent adsorption of the enzyme to an ion exchange resin such as DEAE or TEAE-cellulose). The solution containing the starting reactants is circulated past the immobilized cell or enzyme in direct contact with the enzyme and is thereafter pumped to the electrodialysis cell.

In a further embodiment the enzyme is adsorbed or covalently crosslinked to, or is otherwise immobilized onto the electrodialysis membranes within the electrodialysis cell. For example, the surfaces of the membranes bounding the salt accumulating solution electrodialysis chamber 32a carry charged groups such as sulfonate and tertiary or quaternary amino groups. The enzyme of choice is ionically adsorbed or covalently bound by a conventional cross-linking agent to the salt-accumulating side of the membranes at which the highest local concentration of charged reactants is found. In this embodiment charged reactants are passed into the salt accumulating cells where the enzymes catalytically act on the reactants, the reacted solution passed into the product cells via a peristaltic (non-electrically conductive) pump where charged reactants are removed back into the salt accumulating cells, and the ion depleted product then withdrawn for recovery. In this embodiment the membrane boundary layer of the salt accumulating solution contains a locally elevated concentration of reactant ions, thereby pushing the equilibrium in favor of product, and there is no separate enzyme-reactor loop. However, in this embodiment it is desirable to supply make-up reactants along the length of the salt accumulation chamber, e.g. by a distribution tube inserted into the length of the chamber, so that the reactant concentrations are not reduced at the chamber outflow in comparison to the inflow. Such a reduction would be undesirable because it would tend to result in favoring the hydrolytic direction at the outflow because of reduced reactant concentrations.

While one of the advantages of this invention is the capability of eliminating the need to supply immiscible or miscible organic solvents in the product stream, by no means does the practice of the invention exclude the use of such solvents so long as they are compatible with the enzyme and ion exchange membranes, their subsequent removal is economically viable and, in the case of products intended for administration to animals or humans, they are nontoxic.

We claim:

1. A process of preparing a polypeptide comprising:
   (a) contacting one or more reactants, selected from the group consisting of amino acids, amino acid esters or salts thereof with a protease to produce a composition comprising a mixture of said reactants and one or more polypeptides, provided that if all the reactants together bear substantially zero net ionic charge then all the products together bear a net ionic charge, or if all the products together bear substantially zero net ionic charge then all the reactants together bear a net ionic charge, and provided that the composition is not a fermentation broth;
   (b) electrodialyzing the composition of step (a) whereby product is separated from reactant;
   (c) recovering product; and
   (d) recycling separated reactant into contact with the protease.

2. The process of claim 1 wherein the product is a dipeptide.

3. The process of claim 2 wherein the dipeptide is APM and the reactants are aspartic acid and phenylalanine methyl ester or the salts thereof.

4. The process of claim 1 wherein the protease is capable of acting on substrates to form peptide bonds.

5. The process of claim 1 wherein the protease is an exoprotease capable of catalyzing the formation of a peptide bond between aspartic acid, or its salts, and phenylalanine methyl ester.

6. The process of claim 1 wherein the protease is immobilized by covalent bonding to a support, by physical entrapment or by ionic adsorption.

7. The process of claim 1 wherein the protease is covalently immobilized on the ion exchange membrane.

8. The process of claim 6 wherein the protease is ionically adsorbed onto the membrane.

9. The process of claim 1 wherein the composition further contains an organic solvent.

10. The process of claim 1 wherein the protease is not separated from a reactant solution by a permeable membrane.

* * * * *